(12) United States Patent
Miller

(10) Patent No.: US 8,507,526 B2
(45) Date of Patent: *Aug. 13, 2013

(54) 4-[2-(4-METHYLPHENYLSULFANYL) PHENYL] PIPERIDINE FOR THE TREATMENT OF IRRITABLE BOWEL SYNDROME (IBS)

(75) Inventor: Silke Miller, Thousand Oaks, CA (US)

(73) Assignee: H. Lundbeck A/S, Valby-Copenhagen (DM)

(*) Notice: Subject to any disclaimer, the term of this patent is extended or adjusted under 35 U.S.C. 154(b) by 400 days.

This patent is subject to a terminal disclaimer.

(21) Appl. No.: 12/600,884

(22) PCT Filed: Jun. 13, 2008

(86) PCT No.: PCT/DK2008/000216
§ 371 (c)(1),
(2), (4) Date: Jan. 7, 2010

(87) PCT Pub. No.: WO2008/151632
PCT Pub. Date: Dec. 18, 2008

(65) Prior Publication Data
US 2010/0137366 A1    Jun. 3, 2010

(30) Foreign Application Priority Data
Jun. 15, 2007 (WO) ................ PCT/DK2007/050076

(51) Int. Cl.
*A61K 31/451* (2006.01)
(52) U.S. Cl.
USPC ........................................ 514/317; 546/236

(58) Field of Classification Search
USPC ........................................ 514/317; 546/236
See application file for complete search history.

(56) References Cited

U.S. PATENT DOCUMENTS

| 2005/0014740 A1 | 1/2005 | Ruhland et al. |
| 2009/0264465 A1 | 10/2009 | Bang-Andersen et al. |

FOREIGN PATENT DOCUMENTS

| WO | 03029232 A1 | 4/2003 |
| WO | 2007144006 A1 | 12/2007 |
| WO | WO2008113358 | 9/2008 |
| WO | WO2008113360 | 9/2008 |
| WO | WO2009076962 | * 6/2009 |

OTHER PUBLICATIONS

Thompson et al. "5HT3 receptor as . . . " Exp. Opin. Ther. Targets 11(4) 527-540 (2007).*
PCT-237 (2008).*
Vippagunta et al. "Crystalline solids . . . " Adv. Drug Dil. Rev. 48 p. 3-26 (2001).*
Wikipedia "IBS" p. 1-8,( 2012).*
Wikipedia "Polymorphism" p. 1-3 (2012).*
Wikipedia "Ritonavir" p. 1-3 (2012).*
Creed, F., How do SSRIs help patients with irritable bowel syndrome?, Gut, vol. 55, pp. 1065-1067, 2006.

* cited by examiner

*Primary Examiner* — Celia Chang
(74) *Attorney, Agent, or Firm* — Fish & Richardson P.C.

(57) ABSTRACT

The use of 4-[2-(4-methylphenylsulfanyl)phenyl]piperidine or a pharmaceutically acceptable salt thereof in the treatment of irritable bowl syndrome.

6 Claims, 22 Drawing Sheets

XRPD HBr salt

Figure 1:
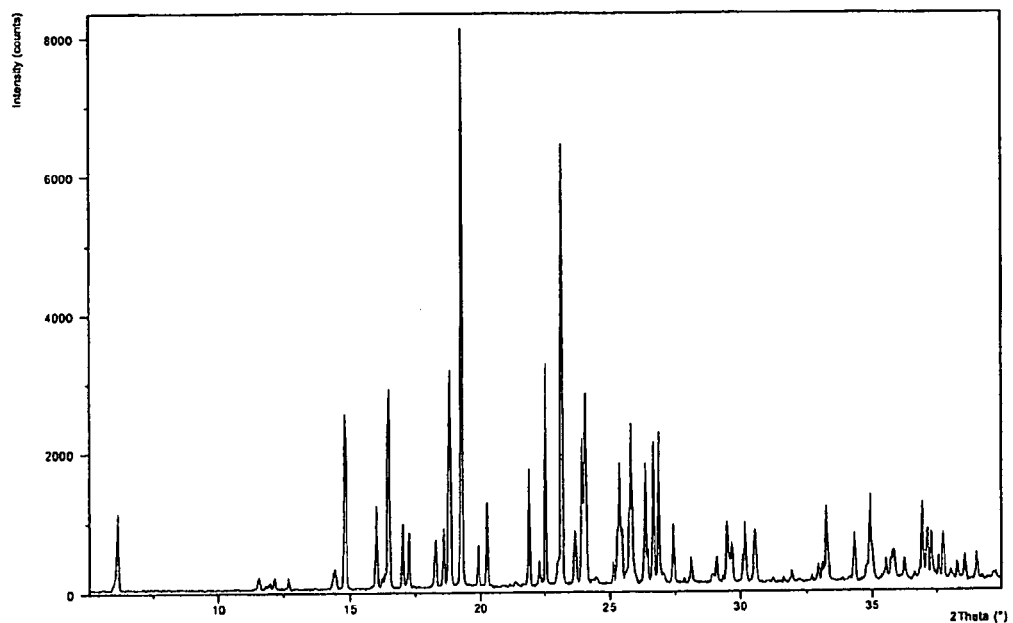

Glutamic acid 1:1 salt + glutamic acid monohydrate

4-[2-(4-METHYLPHENYLSULFANYL) PHENYL] PIPERIDINE FOR THE TREATMENT OF IRRITABLE BOWEL SYNDROME (IBS)

CROSS REFERENCE TO PRIOR APPLICATIONS

This is a U.S. National Phase application under 35 U.S.C. §371 of International Patent Application No. PCT/DK2008/000216, filed Jun. 13, 2008, and claims the benefit of International Patent Application No. PCT/DK2007/050076, filed Jun. 15, 2007 both of which are incorporated by reference herein. International Patent Application No. PCT/DK2008/000216 published in English on Dec. 18, 2008 as WO 2008/151632 under PCT Article 21(2).

FIELD OF THE INVENTION

The present invention provides the use of 4-[2-(4-methylphenylsulfanyl)-phenyl]piperidine for the treatment of irritable bowl syndrome (IBS).

BACKGROUND

Irritable bowl syndrome is a chronic disorder of the intestines causing bloating, abdominal pain, constipation and/or diarrhoea. The symptoms of IBS have not been explained by anatomical or metabolic abnormalities. Rather, IBS is considered to be a biopsychosocial disorder resulting from a combination of three interacting mechanisms, i.e. altered bowl motility, increased visceral sensitivity, and psychosocial factors [*Gastroenterol.*, 120, 652-668, 2001].

Irritable bowl disease is a common disease mainly effecting women and with an estimated prevalence in Europe and North America of 10-15%. The disease is, however, not well recognised and only a fraction of those subjects affected by the disease is actually formally diagnosed. The prevalence of patients diagnosed with IBS in eight European countries is only 2.8% in average [*Aliment. Pharmacol. Ther.*, 24, 183-205, 2006].

Irritable bowl syndrome is normally divided into three subgroups defined by the predominant bowl habit, i.e. constipation-predominant (c-IBS), diarrhoea-predominant (d-IBS) and IBS with alternating symptoms of both constipation and diarrhoea (a-IBS).

Irritable bowl syndrome is being treated with various therapeutic agents including antispasmodics, laxatives, anti-diarrhoea agents, tri-cyclic antidepressants and $5\text{-HT}_3$ antagonists. Odansetron is a $5\text{-HT}_3$ antagonist, and the compound has in clinical trials been shown to improve stool consistency, bowel frequency and reduce the number of pain episodes. Alosetron, which is also a $5\text{-HT}_3$ antagonist, has been shown to improve abdominal pain or discomfort and faecal urgency [*Aliment. Pharmacol. Ther.*, 24, 183-205, 2006]. Alosetron is licensed by the FDA for the treatment of women with severe diarrhoea-predominant IBS.

The compound 4-[2-(4-methylphenylsulfanyl)phenyl]piperidine was first disclosed in the international patent application published as WO 2003/029232 wherein the compound was shown to be a serotonin transport inhibitor. Later, in the international patent application published as WO 2007/144006 crystalline salts of said compound was disclosed together with a more extensive pharmacological profile including $5\text{-HT}_3$ antagonism.

SUMMARY OF THE INVENTION

In on embodiment, the invention relates to a method for the treatment of irritable bowl syndrome (IBS), the method comprising the administration of a therapeutically effective amount of 4-[2-(4-methylphenylsulfanyl)phenyl]piperidine or a therapeutically acceptable salts thereof (hereafter compound I) to a patient in need thereof.

In one embodiment, the invention provides compound I for use in the treatment of IBS.

In one embodiment, the invention provides the use of compound I in the manufacture of a medicament for the treatment of IBS.

FIGURES

FIG. 1: X-ray diffraction pattern of the HBr addition salt of compound I

Figure 2:
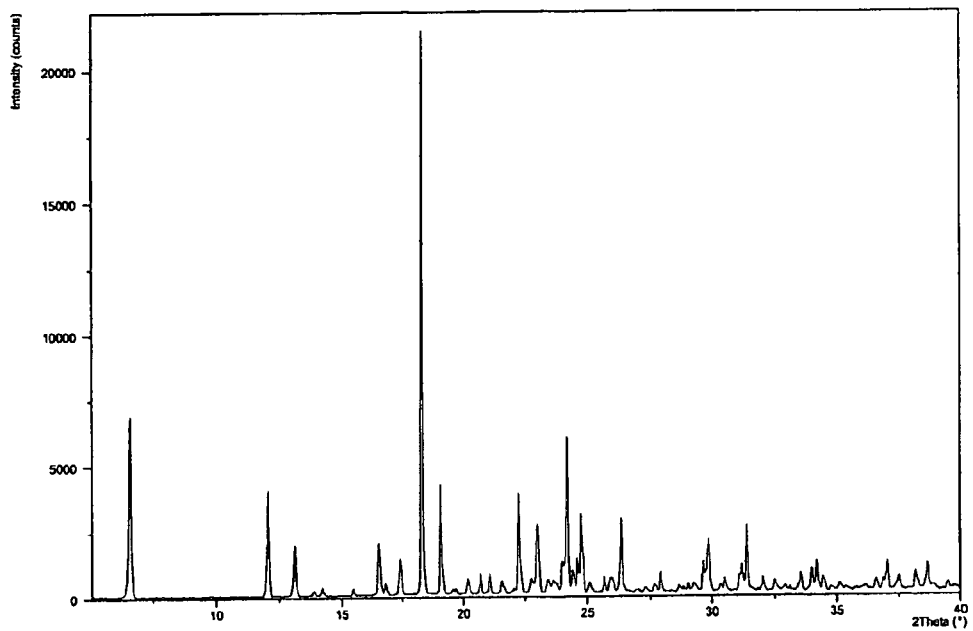
Figure 3:
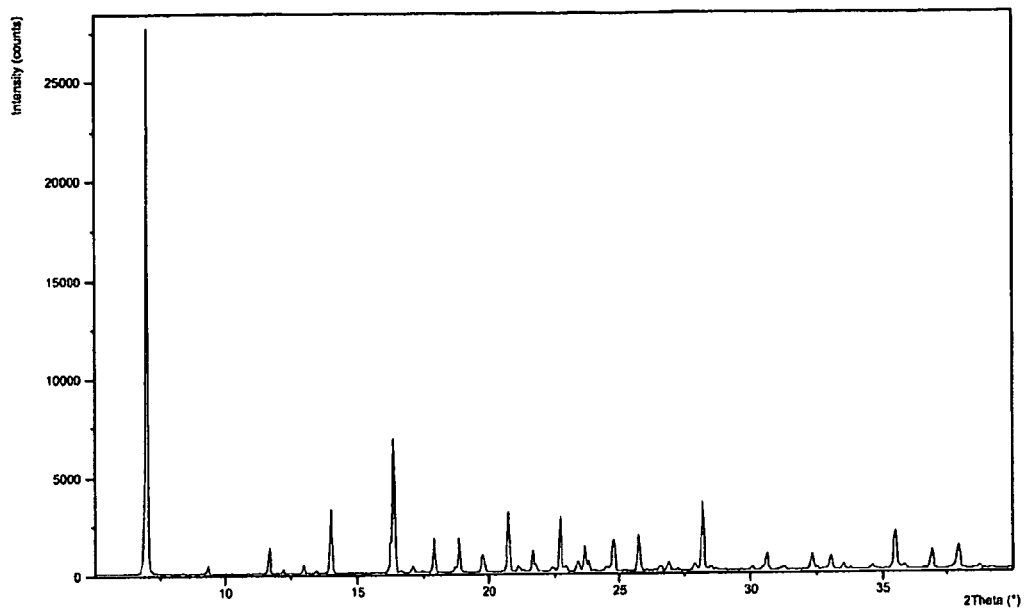

FIG. 2: X-ray diffraction pattern of the HBr addition salt solvate of compound I FIG. 3: X-ray diffraction pattern of the palmitic acid addition salt of compound I FIG. 4: X-ray diffraction pattern of the DL-lactic acid addition salt of compound I FIG. 5: X-ray diffraction pattern of the adipic acid addition salt (1:1) of compound I (α-β form)

Figure 6:
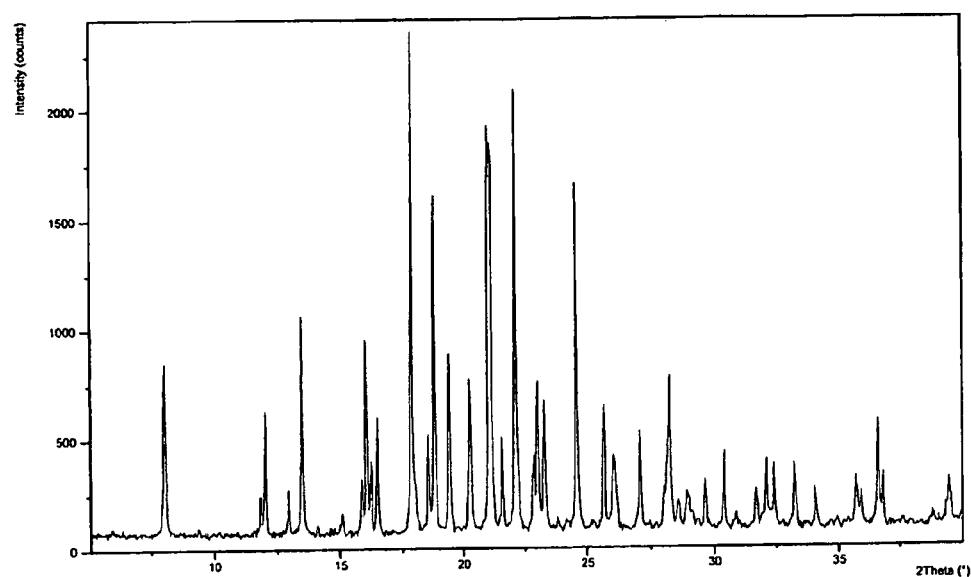
Figure 7:
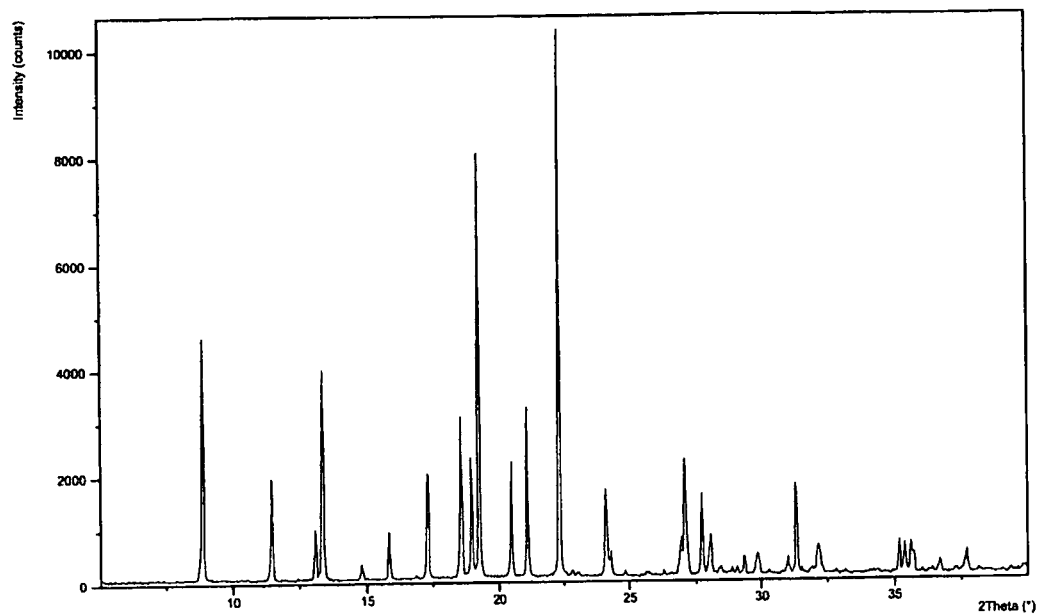
Figure 11:
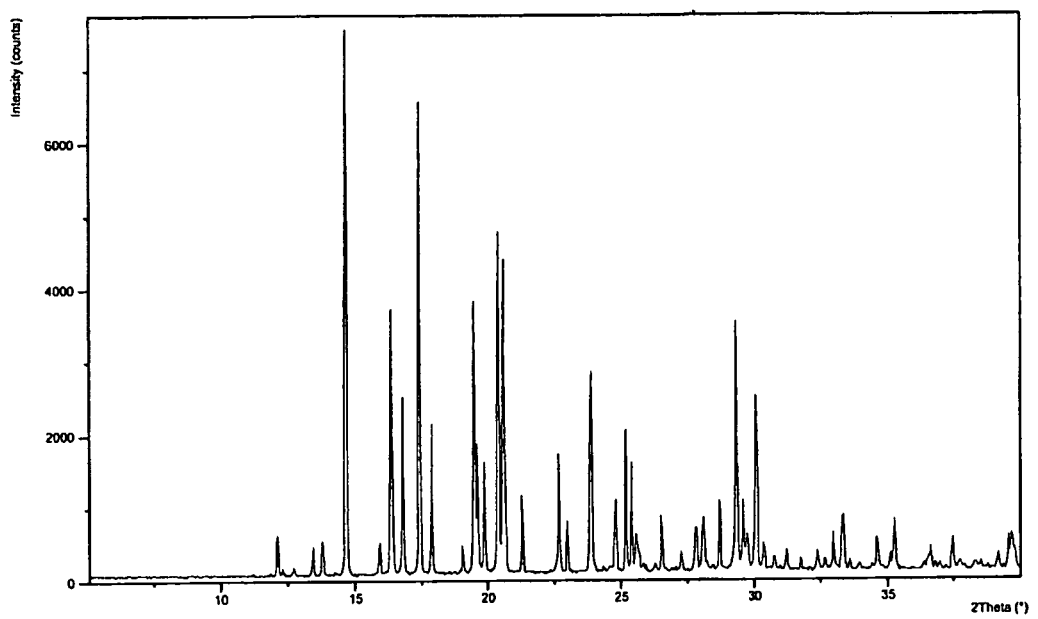
Figure 12:
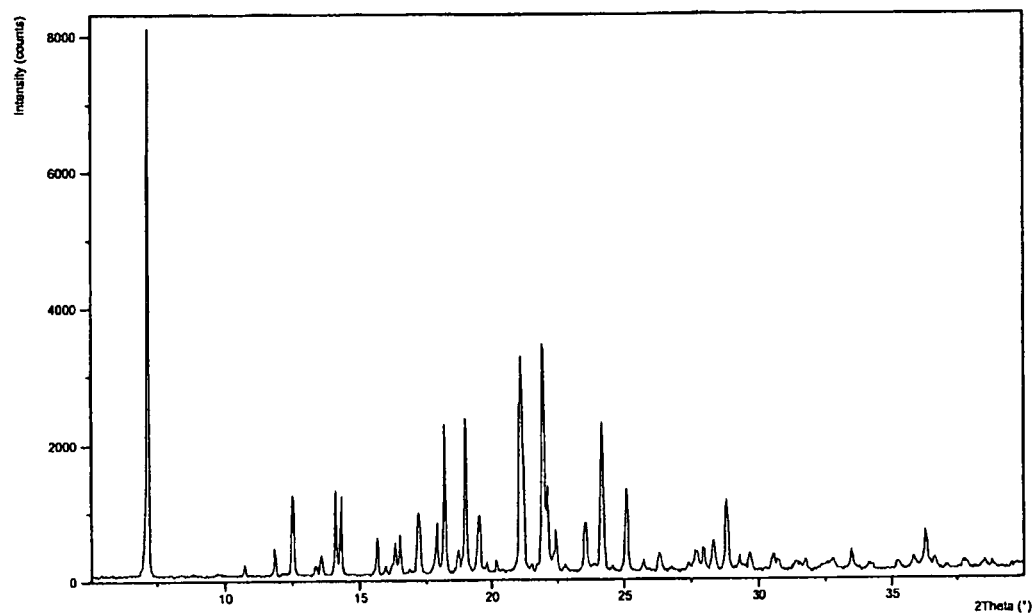
Figure 13:
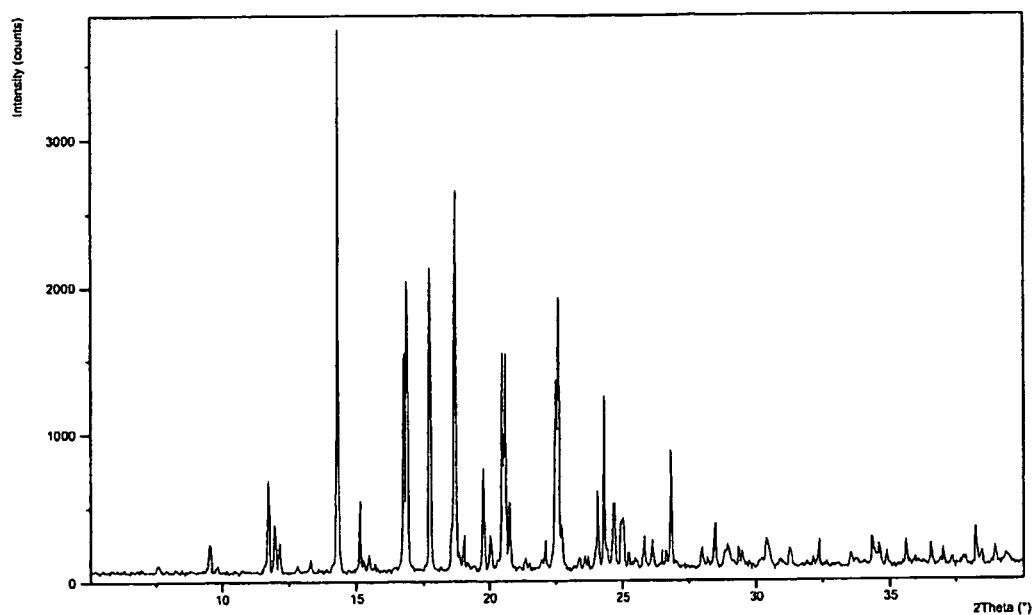
Figure 14:
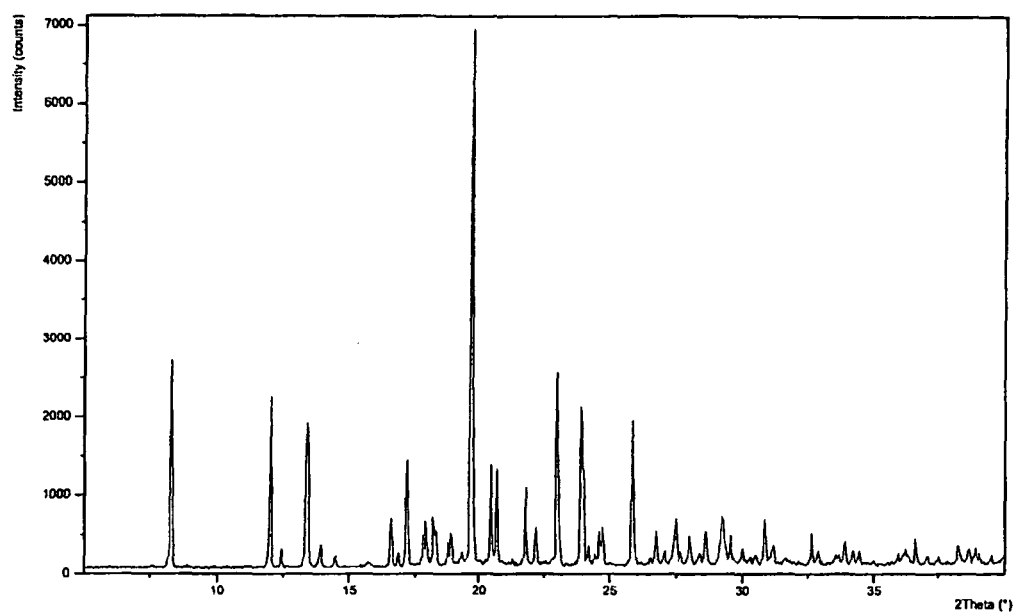
Figure 15:
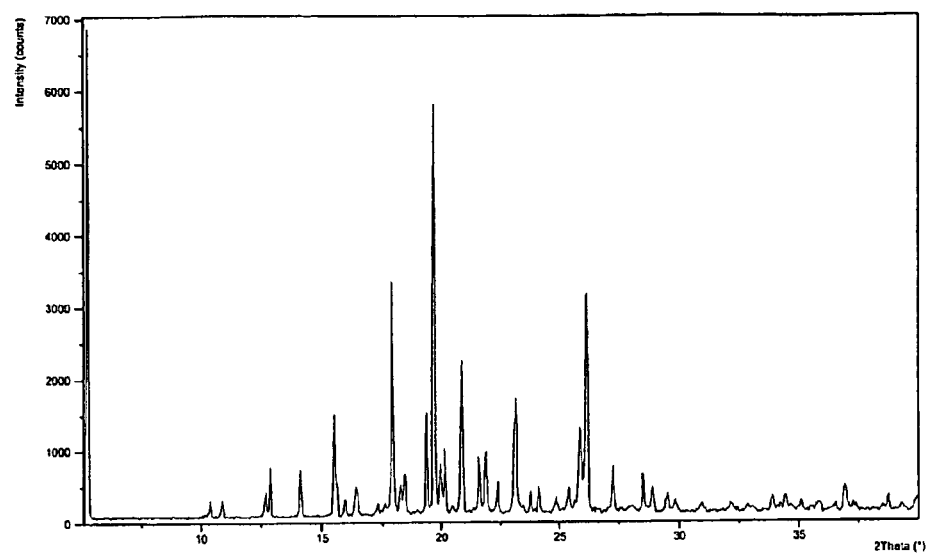
Figure 16:
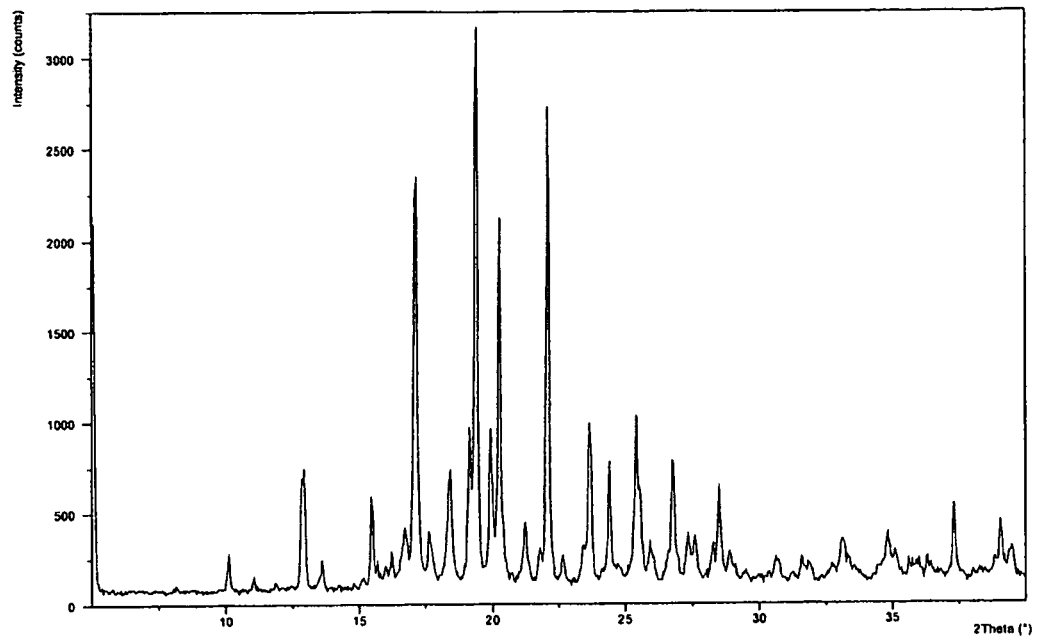
Figure 20:
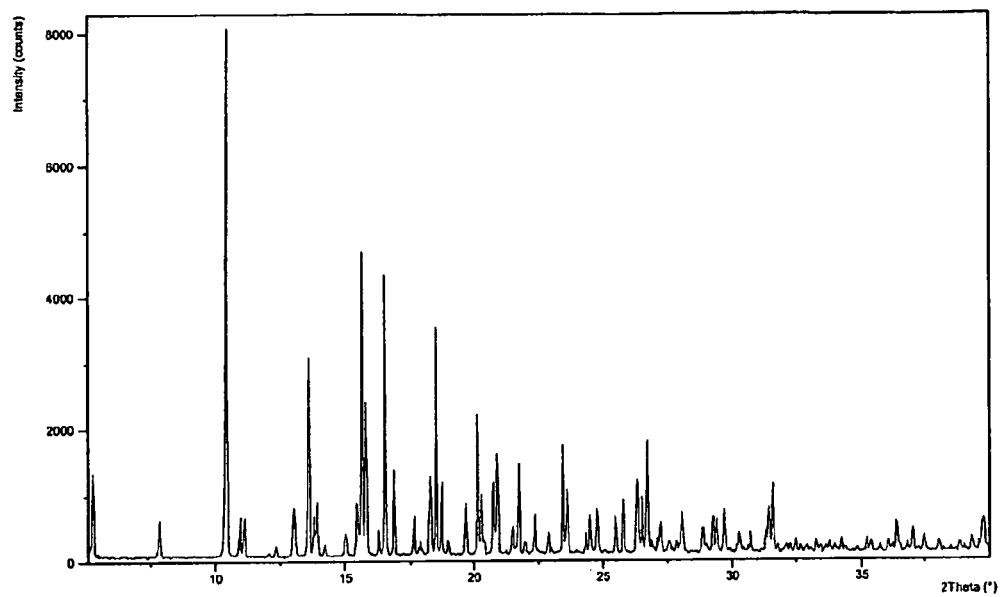
Figure 21:
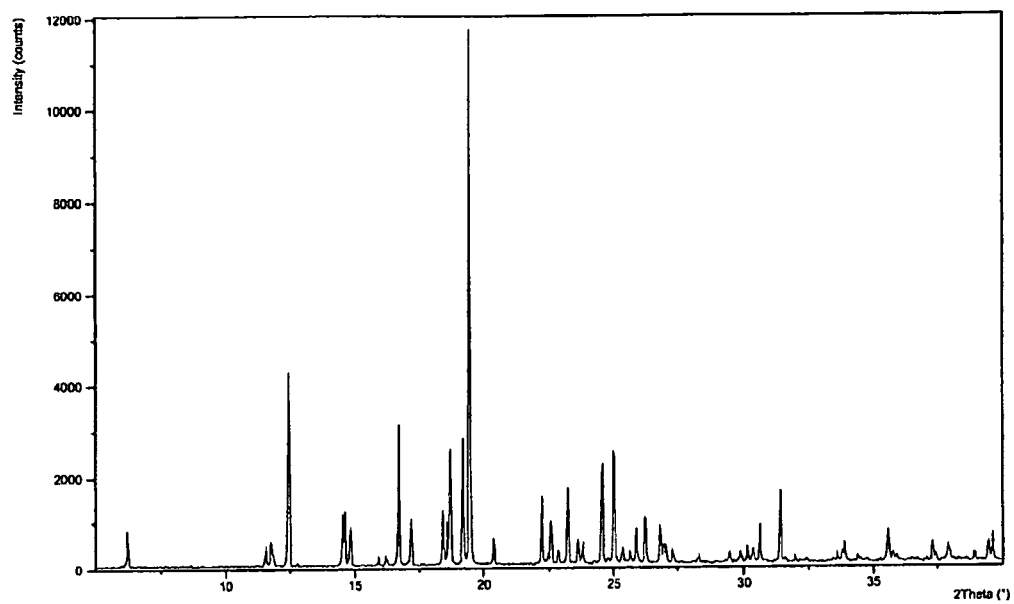
Figure 22:
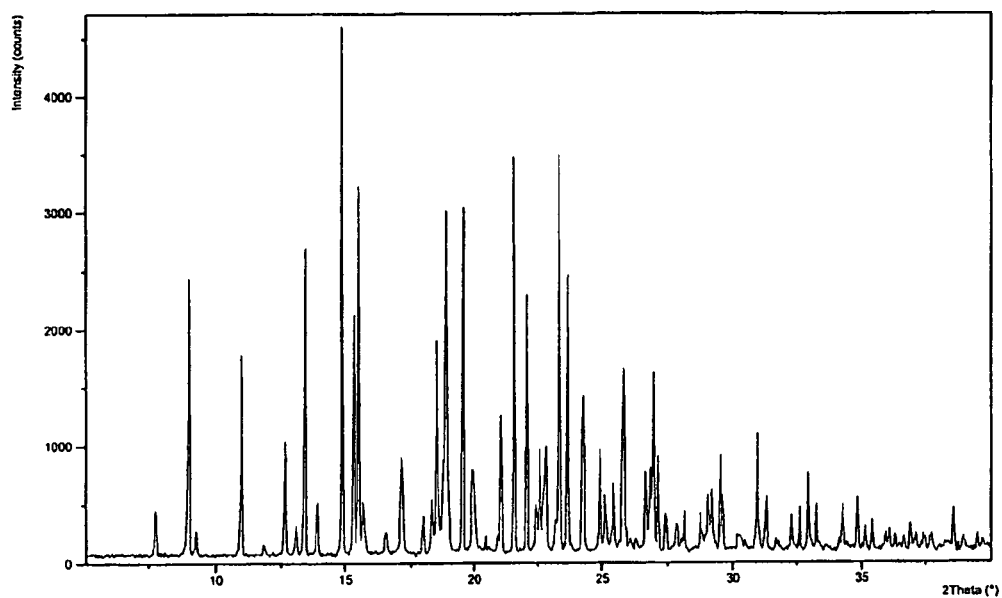

FIG. 6: X-ray diffraction pattern of the adipic acid addition salt (2:1) of compound I FIG. 7: X-ray diffraction pattern of the fumaric acid addition salt (1:1) of compound I FIG. 8: X-ray diffraction pattern of the glutaric acid addition salt (1:1) of compound I FIG. 9: X-ray diffraction pattern of the malonic acid addition salt (1:1) of compound I, α-form FIG. 10: X-ray diffraction pattern of the malonic acid addition salt of compound I, β-form FIG. 11: X-ray diffraction pattern of the oxalic acid addition salt (1:1) of compound I FIG. 12: X-ray diffraction pattern of the sebacoinic acid addition salt (2:1) of compound I FIG. 13: X-ray diffraction pattern of the succinic acid addition salt (2:1) of compound I FIG. 14: X-ray diffraction pattern of the L-malic acid addition salt (1:1) of compound I, α-form FIG. 15: X-ray diffraction pattern of the L-malic acid addition salt (1:1) of compound I, β-form FIG. 16: X-ray diffraction pattern of the D-tartaric acid addition salt (1:1) of compound I FIG. 17: X-ray diffraction pattern of the L-aspartic acid addition salt (1:1) of compound I in mixture with L-aspartic acid FIG. 18: X-ray diffraction pattern of the L-aspartic acid addition salt hydrate (1:1) of compound I in mixture with L-aspartic acid FIG. 19: X-ray diffraction pattern of the glutamic acid addition salt (1:1) of compound I in mixture with glutamic acid monohydrate FIG. 20: X-ray diffraction pattern of the citric acid addition salt (2:1) of compound I FIG. 21: X-ray diffraction pattern of the HCl acid addition salt of compound I FIG. 22: X-ray diffraction pattern of the phosphoric acid addition salt (1:1) of compound I

DETAILED DESCRIPTION OF THE INVENTION

The structure of 4-[2-(4-methylphenylsulfanyl)-phenyl]piperidine is

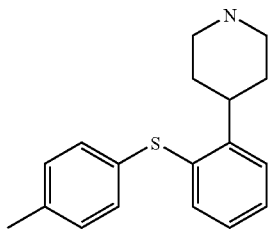 [SMILES: Cc1ccc(Sc2ccccc2C2CCNCC2)cc1]

In one embodiment, the pharmaceutically acceptable salts used in the present invention are acid addition salts of acids that are non-toxic. Said salts include salts made from organic acids, such as maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, malonic, mandelic, cinnamic, citraconic, aspartic, stearic, palmitic, itaconic, glycolic, p-aminobenzoic, glutamic, benzenesulfonic, theophylline acetic acids, as well as the 8-halotheophyllines, for example 8-bromotheophylline. Said salts may also be made from inorganic salts, such as hydrobromic, sulfuric, sulfamic, phosphoric and nitric acids. Additional useful salts are listed in the table in example 1d (table 1).

In one embodiment, compound I is the HBr addition salt

In one embodiment, compound I is the DL-lactic acid addition salt, and in particular the 1:1 salt.

In one embodiment, compound I is the L-aspartic acid addition salt, and in particular the 1:1 salt.

In one embodiment, compound I is the glutamic acid addition salt, and in particular the 1:1 salt.

In one embodiment, compound I is the glutaric acid addition salt, and in particular the 1:1 salt.

In one embodiment, compound I is the malonic acid addition salt, and in particular the 1:1 salt that is found to exist in two polymorphic modifications α and β of which the 3 form is believed to be the most stable based on a lower solubility.

In one embodiment, compound I is in a purified form. The term "purified form" is intended to indicate that the compound is essentially free of other compounds or other forms, i.e. polymorphs of said compound, as the case may be.

Oral dosage forms, and in particular tablets and capsules, are often preferred by the patients and the medical practitioner due to the ease of administration and the consequently better compliance. For tablets and capsules, it is preferable that the active ingredients are crystalline.

Crystals of compound I may exist as solvates, i.e. crystals wherein solvent molecules form part of the crystal structure. The solvate may be formed from water, in which case the solvates are often referred to as hydrates. Alternatively, the solvates may be formed from other solvents, such as e.g. ethanol, acetone, or ethyl acetate. The exact amount of solvate often depends on the conditions. For instance, hydrates will typically loose water as the temperature is increased or as the relative humidity is decreased. Compounds, which do not change or which change only little when conditions, such as e.g. humidity change are generally regarded as better suited for pharmaceutical formulations. It is noted that the HBr addition salt does not form hydrates when precipitated from water whereas compounds such as the succinate, malate and tatrate acid addition salts do.

Some compounds are hygroscopic, i.e. they absorb water when exposed to humidity. Hygroscopicity is generally regarded as an undesired property for compounds, which are to be presented in a pharmaceutical formulation, in particular in a dry formulation, such as tablets or capsules. In one embodiment, the invention uses crystals with low hygroscopicity.

For oral dosage forms using crystalline active ingredients it is also beneficial if said crystals are well-defined. In the present context, the term "well-defined" in particular means that the stoichiometry is well-defined, i.e. that the ratio between the ions forming the salt is the ratio between small integers, such as 1:1, 1:2, 2:1, 1:1:1, etc. In one embodiment, the compounds used in the present invention are well-defined crystals.

The solubility of an active ingredient is also of significance for the choice of dosage form as it may have a direct impact on bio-availability. For oral dosage forms, a higher solubility of the active ingredient is generally believed to be beneficial as it increases the bio-availability. Some patients, e.g. elderly patients may have difficulties swallowing tablets, and oral drop solutions may be a suitable alternative avoiding the need for swallowing tablets. In order to limit the volume of an oral drop solution, it is necessary to have a high concentration of the active ingredient in the solution, which again requires a high solubility of the compound. As shown in table 3, DL-lactic acid, L-aspartic acid, glutamic acid, glutaric acid and malonic acid addition salts have exceptionally high solubility.

Crystal forms impact the filtration and processing properties of a compound. Needle formed crystals tend to be more difficult to handle in a production environment as filtration becomes more difficult and time consuming. The exact crystal form of a given salt may depend e.g. on the conditions under which the salt was precipitated. The HBr acid addition salt used in the present invention grows needle-shaped, solvated crystals when precipitated from ethanol, acetic acid and propanol, but crystals of a non-hydrated form, which are not needle-shaped, when HBr addition salt is precipitated from water, providing superior filtration properties.

Table 3 also depicts the Resulting pH, i.e. the pH in the saturated solution of the salt. This property is of importance because moisture can never be completely avoided during storage and the accumulation of moisture will give rise to a pH decrease in or on a tablet comprising a low Resulting pH salt, which may decrease shell life. Moreover, a salt with a low resulting pH may give rise to corrosion of process equipment if tablets are made by wet granulation. The data in table 3 suggest that the HBr, HCl and adipic acid addition salts may be superior in this respect.

In one embodiment, the compound I is the HBr addition salt in a crystalline form, in particular in a purified form. In a further embodiment, said HBr salt has peaks in an X-ray powder diffractogram (XRPD) at approximately 6.08°, 14.81°, 19.26° and 25.38°2θ, and in particular said HBr salt has an XRPD as depicted in FIG. 1.

Figure 4:
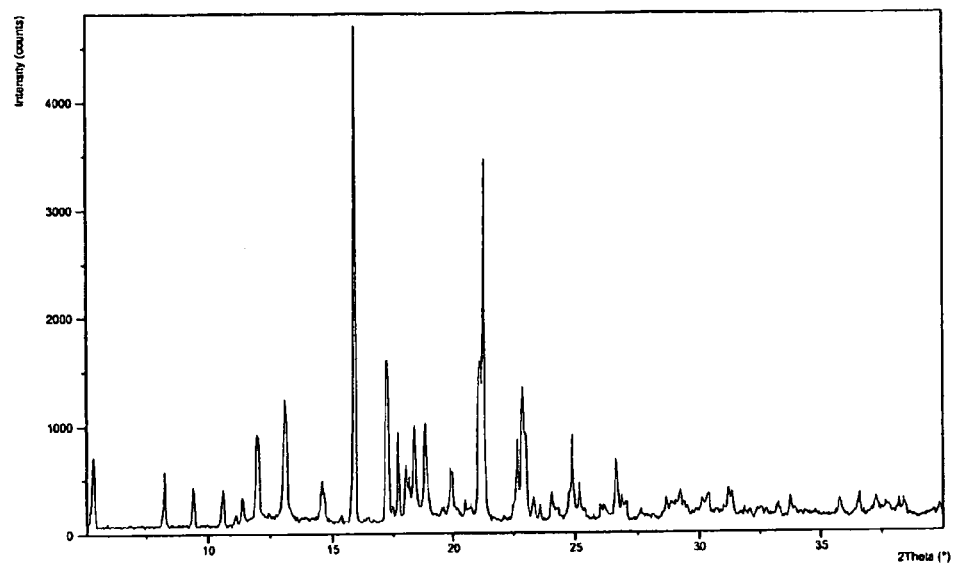
Figure 5:
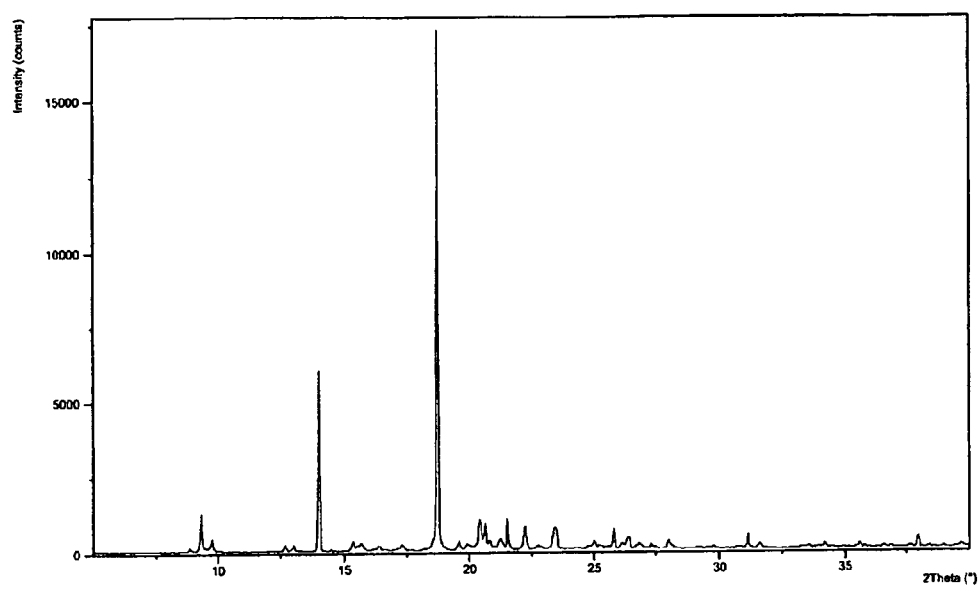

In one embodiment, the compound I is the DL-lactic acid addition salt (1:1) in a crystalline form, in particular in a purified form. In a further embodiment, said DL-lactic acid addition salt has peaks in a XRPD at approximately 5.30°, 8.81°, 9.44° and 17.24°2θ, and in particular said DL lactic acid addition salt has an XRPD as depicted in FIG. 4.

Figure 17:
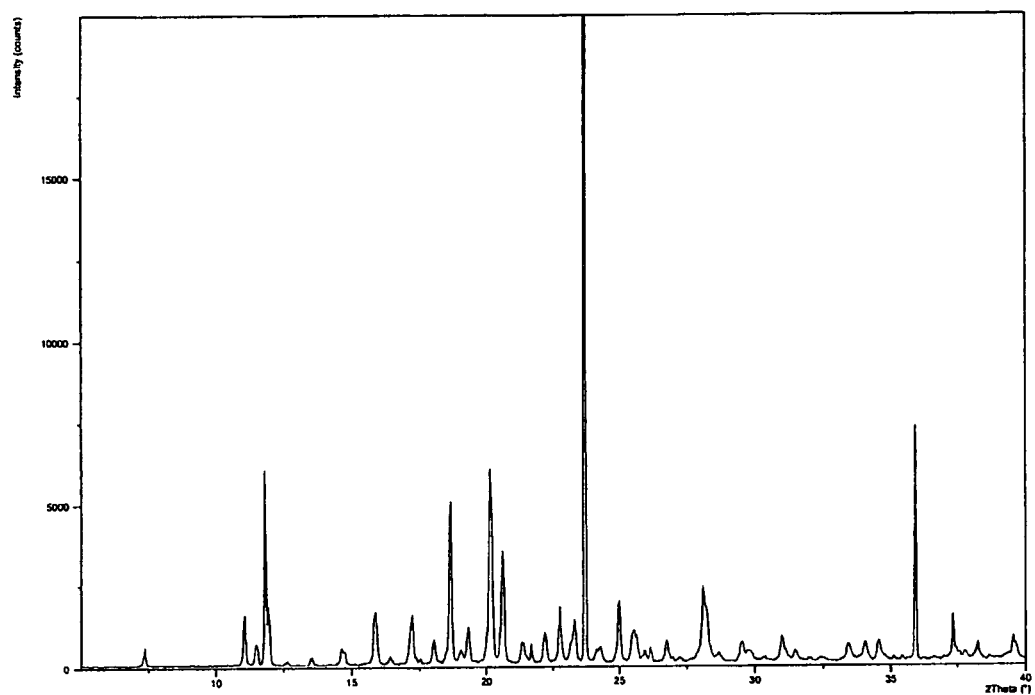
Figure 18:
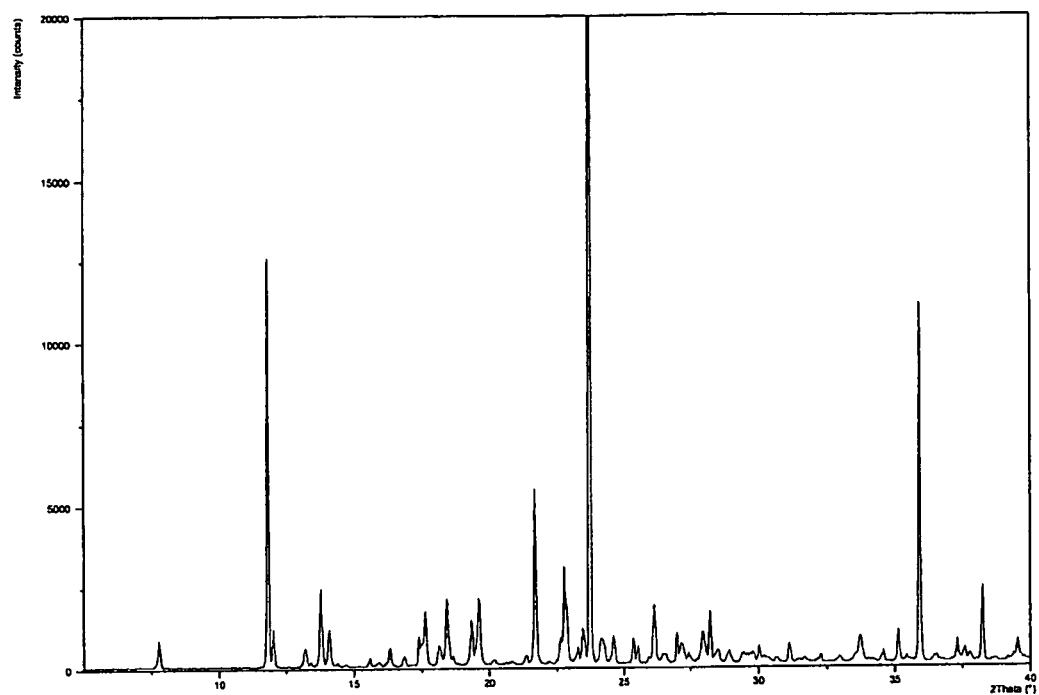

In one embodiment, the compound I is the L-aspartic acid addition salt (1:1) in a crystalline form, in particular in a purified form. In a further embodiment, said L-aspartic acid addition salt is unsolvated and has peaks in a XRPD at approximately 11.05°, 20.16°, 20.60°, 25.00°2θ, and in particular said L-aspartic salt, when mixed with L-aspartic acid, has an XRPD as depicted in FIG. 17. In one embodiment, said L-aspartic acid addition salt is a hydrate, in particular in a purified form. In a further embodiment, said L-aspartic acid addition salt hydrate has peaks in a XRPD at approximately 7.80°, 13.80°, 14.10°, 19.63°2θ, and in particular said L-aspartic addition salt hydrate, when mixed with L-aspartic acid, has an XRPD as depicted in FIG. 18.

Figure 19:
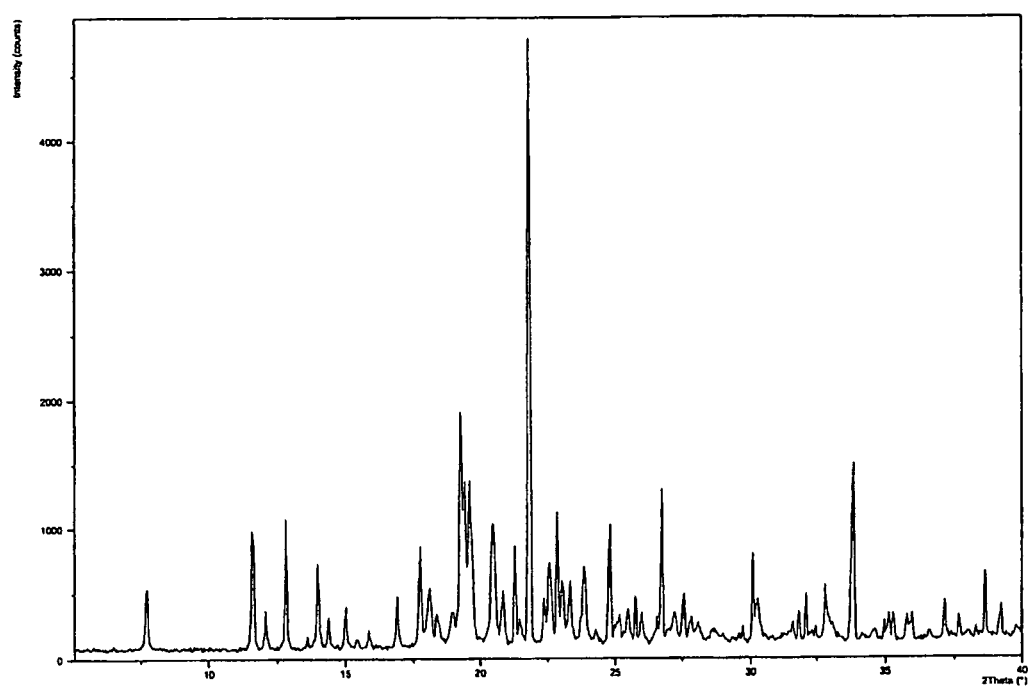

In one embodiment, the compound I is the glutamic acid addition salt (1:1) in a crystalline form, in particular in a purified form. In a further embodiment, said glutamic acid addition salt has peaks in a XRPD at approximately 7.71°, 14.01°, 19.26°, 22.57°2θ, and in particular said glutamic acid salt, when mixed with glutamic acid monohydrate, has an XRPD as depicted in FIG. 19.

Figure 9:
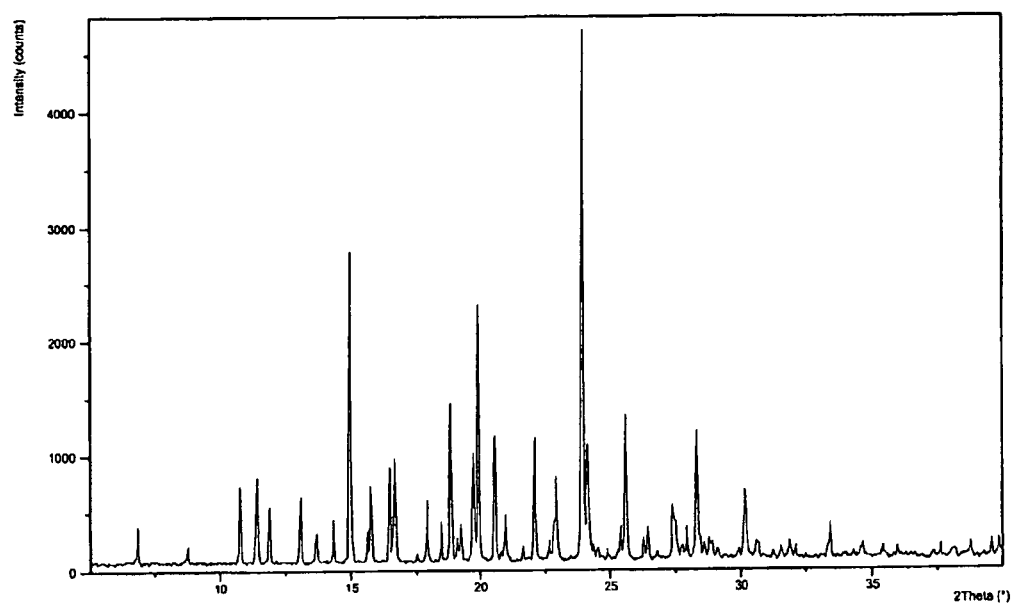
Figure 10:
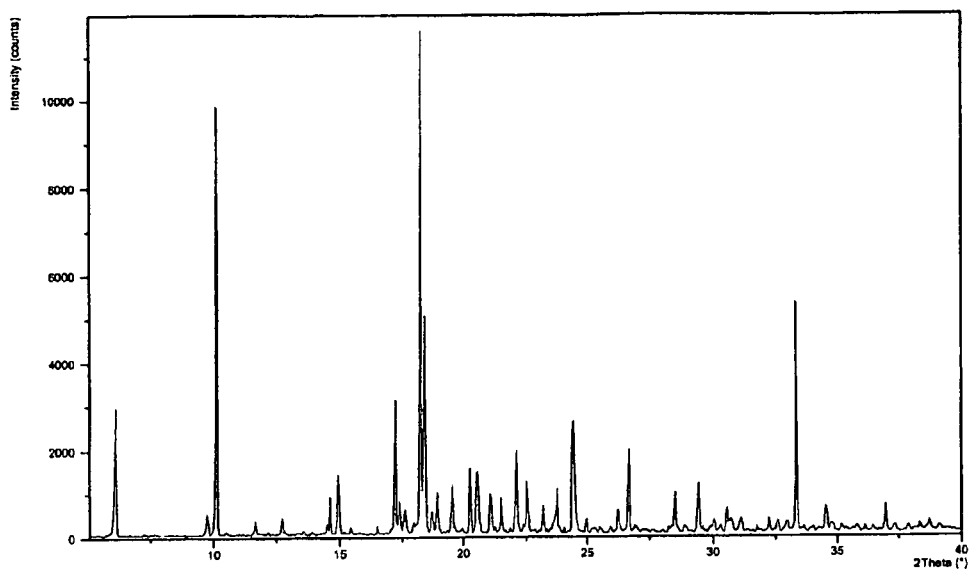

In one embodiment, the compound I is the malonic acid addition salt (1:1) in a crystalline form, in particular in a purified form. In a further embodiment, said malonic acid addition salt is the α-form and has peaks in a XRPD at approximately 10.77°, 16.70°, 19.93°, 24.01°2θ, or said malonic acid addition salt is the β-form and has peaks in a XRPD at approximately 6.08°, 10.11°, 18.25°, 20.26°2θ and in particular said malonic acid addition salt has an XRPD as depicted in FIG. 9 or 10.

Figure 8:
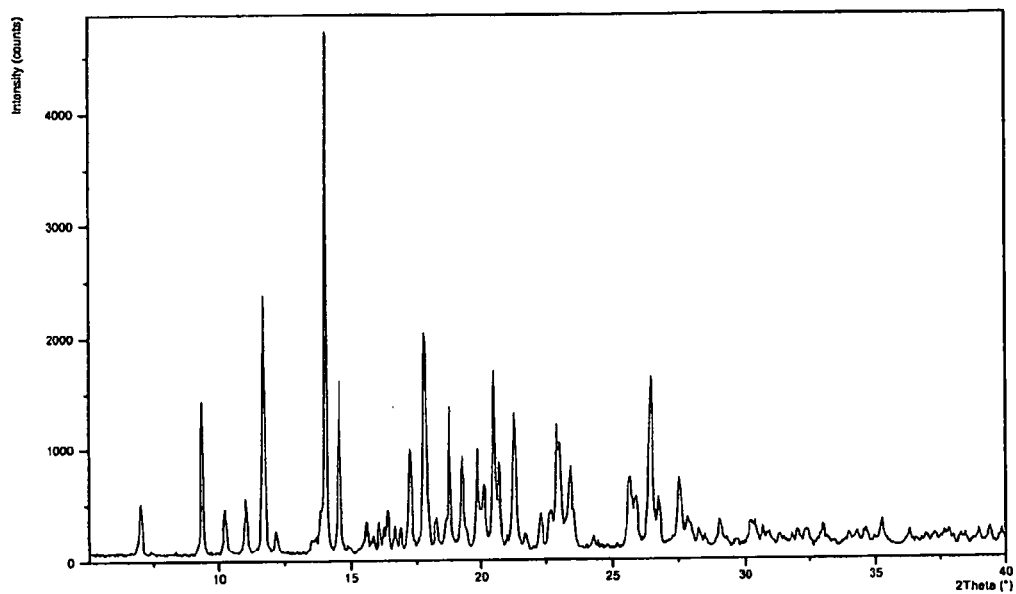

In one embodiment, the compound I is the glutaric acid addition salt (1:1) in a crystalline form, in particular in a purified form. In a further embodiment, said glutaric acid addition salt has peaks in a XRPD at approximately 9.39°, 11.70°, 14.05°, and 14.58°2θ, and in particular said glutaric acid addition salt has an XRPD as depicted in FIG. 8.

The pharmacological profile of the compound I is discussed in the international application published as WO 2007/144006, but can be summarised as follows. The compound is inhibitor of the serotonin and norepinephrine reuptake; inhibitor of the serotonin receptors 2A, 2C and 3; and inhibitor the α-1 adrenergic receptor.

Due to the potent inhibition of the 5-HT$_3$ receptor, compound I is believed to be useful in the treatment of IBS. As shown in the examples, compound I also has a strong effect on pain, which as discussed above is a prominent symptom of IBS.

In an embodiment, the compound I is administered in an amount of about 0.001 to about 100 mg/kg body weight per day.

A typical oral dosage is in the range of from about 0.001 to about 100 mg/kg body weight per day, preferably from about 0.01 to about 50 mg/kg body weight per day, administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

A typical oral dosage for adults is in the range of 1-100 mg/day of compound I, such as 1-30 mg/day, or 5-25 mg/day. This may typically be achieved by the administration of 0.1-50 mg, such as 1-25 mg, such as 1, 5, 10, 15, 20 or 25 mg of compound I once or twice daily.

A "therapeutically effective amount" of a compound as used herein means an amount sufficient to cure, alleviate or partially arrest the clinical manifestations of a given disease and its complications in a therapeutic intervention comprising the administration of said compound. An amount adequate to accomplish this is defined as "therapeutically effective amount". The term also includes amounts sufficient to cure, alleviate or partially arrest the clinical manifestations of a given disease and its complications in a treatment comprising the administration of said compound. Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatments are two separate aspect of the invention. The patient to be treated is preferably a mammal, in particular a human being. In particular, the patient to be treated has been diagnosed with IBS.

Compound I may be administered alone as a pure compound or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, cremes, gels, inhalants, dermal patches, implants, etc.

Conveniently, compound I is administered in a unit dosage form containing said compounds in an amount of about 0.1 to 50 mg, such as 1 mg, 5 mg 10 mg, 15 mg, 20 mg or 25 mg of compound I.

For parenteral routes such as intravenous, intrathecal, intramuscular and similar administration, typically doses are in the order of about half the dose employed for oral administration.

For parenteral administration, solutions of compound I in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. The pharmaceutical compositions formed by combining compound I and the pharmaceutical acceptable carriers are then readily administered in a variety of dosage forms suitable for the disclosed routes of administration.

Formulations used in the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule in powder or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by the compression of the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Capsules comprising a compound of the present invention may be prepared by mixing a powder comprising said compound with microcrystalline cellulose and magnesium stearate and place said powder in a hard gelatine capsule. Optionally, said capsule may be coloured by means of a suitable pigment. Typically, capsules will comprise 0.25-20% of a compound of the present invention, such as 0.5-1.0%, 3.0-4.0%, 14.0-16.0% of a compound of the present invention. These strengths can be used to conveniently deliver 1, 5, 10, 15, 20 and 25 mg of a compound of the present invention in a unit dosage form.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

Compound I may be prepared as outlined in WO 2003/029232 or WO 2007/144006. Salts of compound I may by addition of an appropriate acid followed by precipitation. Precipitation may be brought about by e.g. cooling, removal of solvent, addition of another solvent or a mixture thereof.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to Cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

Analytical Methods

X-Ray powder diffractograms (XRPD) were measured on a PANalytical X'Pert PRO X-Ray Diffractometer using $CuK_{\alpha 1}$ radiation. The samples were measured in reflection mode in the 2θ-range 5-40° using an X'celerator detector.

Elemental composition (CHN) was measured on an Elementar Vario EL instrument from Elementar. About 4 mg of sample was used for each measurement, and the results are given as mean values of two measurements.

Example 1a

HBr Salt of Compound I

To 442 grams of stirred and slightly heated (approx. 45° C.) 4-(2-p-Tolylsulfanyl-phenyl)-piperidine-1-carboxylic acid ethyl ester as an oil was added 545 ml of 33 wt-% HBr in AcOH (5.7 M, 2.5 eqv.). This mixing gives a 10° C. exotherm. After final addition the reaction mixture is heated to 80° C. and left for 18 hours. A sample is withdrawn and analysed by HPLC and if not completed more 33 wt-% HBr in AcOH must be added. Otherwise the mixture is cooled to 25° C. making the product 4-(2-p-Tolylsulfanyl-phenyl)-piperidine hydrobromide to precipitate. After one hour at 25° C. the thick suspension is added 800 ml diethylether. Stirring is continued for another hour before the product is isolated by filtration, washed with 400 ml diethylether and dried in vacuum at 40° C. overnight. The hydrobromide of compound I was isolated as white solid.

Example 1b

HBr Salt of Compound I 2-(4-tolylsulfanyl)-phenyl bromide

In a stirred nitrogen covered reactor N-methyl-pyrrolidone, NMP (4.5 L) was flushed with nitrogen for 20 minutes. 4-Methylbenzenethiol (900 g, 7.25 mol) was added and then 1,2-dibromobenzene (1709 g, 7.25 mol). Potassium tert-butoxide (813 g, 7.25 mol) was finally added as the last reactant. The reaction was exothermic giving a temperature rise of the reaction mixture to 70° C. The reaction mixture was then heated to 120° C. for 2-3 hours. The reaction mixture was cooled to room temperature. Ethyl acetate (4 L) was added and aqueous sodium chloride solution (15%, 2.5 L). The mixture was stirred for 20 minutes. The aqueous phase was separated and extracted with another portion of ethyl acetate (2 L). The aqueous phase was separated and the organic phases were combined and washed with sodium chloride solution (15%, 2.5 L). The organic phase was separated, dried with sodium sulphate and evaporated at reduced pressure to a red oil which contains 20-30% NMP. The oil was diluted to twice the volume with methanol and the mixture was refluxed. More methanol was added until a clear red solution was obtained. The solution was cooled slowly to room temperature while seeded. The product crystallises as off white crystals, they were isolated by filtration and washed with methanol and dried at 40° C. in a vacuum oven until constant weight.

Ethyl 4-hydroxy-4-(2-(4-tolylsulfanyl)phenyl)-piperidin-1-carboxylate

In a stirred reactor under nitrogen cover 2-(4-tolylsulfanyl)-phenyl bromide (600 g, 2.15 mol) was suspended in heptane (4.5 L). At room temperature 10M BuLi in hexane (235 mL, 2.36 mol) was added over 10 minutes. Only a small exotherm was noticed. The suspension was stirred for 1 hour at ambient temperature and then cooled down to −40° C. 1-Carbethoxy-4-piperidone (368 g, 2.15 mol) dissolved in THF (1.5 L) was added at a rate not faster than the reaction temperature was kept below −40° C. When the reaction has gone to completion, it was warmed to 0° C. and 1M HCl (1 L) was added keeping the temperature below 10° C. The acid aqueous phase was separated and extracted with ethyl acetate (1 L). The organic phases were combined and extracted with sodium chloride solution (15%, 1 L). The organic phase was dried over sodium sulphate and evaporated to a semi crystalline mass. It was slurried with ethyl ether (250 mL) and filtered off. Dried in a vacuum oven at 40° C. until constant weight.

Ethyl 4-(2-(4-tolylsulfanyl)phenyl)-piperidin-1-carboxylate

Trifluoroacetic acid (2.8 kg, 24.9 mol) and triethylsilane (362 g, 3.1 mol) was charged in a reactor with an efficient stirrer. Ethyl 4-hydroxy-4-(2-(4-tolylsulfanyl)phenyl)-piperidin-1-carboxylate (462 g, 1.24 mol) was added via a powder funnel in portions. The reaction was slightly exothermic. The temperature rose to 50° C. After the addition was finalised the reaction mixture was warmed to 60° C. for 18 hours. The reaction mixture was cooled down to room temperature. Toluene (750 mL) and water (750 mL) was added. The organic phase was isolated and the aqueous phase was extracted with another portion of toluene (750 mL). The organic phases were combined and washed with sodium chloride solution (15%, 500 mL) and dried over sodium sulphate. The sodium sulphate was filtered off, the filtrate evaporated at reduced pressure to a red oil, which was processed further in the next step.

4-(2-(4-tolylsulfanyl)phenyl)-piperidin hydrobromide

The crude ethyl 4-(2-(4-tolylsulfanyl)phenyl)-piperidin-1-carboxylate as a red oil from example 3 was mixed in a stirred reactor with hydrobromic acid in acetic acid (40%, 545 mL, 3.11 mol). The mixture was heated at 80° C. for 18 hours. The reaction mixture was cooled down to room temperature. During the cooling the product crystallises out. After 1 hour at room temperature ethyl ether (800 mL) was added to the reaction mixture, and the mixture was stirred for another hour. The product was filtered off, washed with ethyl ether and dried in a vacuum oven at 50° C. until constant weight.

Example 1c

Recrystallisation of the HBr Salt of Compound

A mixture of 10.0 grams of the HBr salt of compound I, e.g. prepared as above, was heated to reflux in 100 ml H$_2$O. The mixture became clear and fully dissolved at 80-90° C. To the clear solution was added 1 gram of charcoal and reflux was continued for 15 minutes before filtered and left to cool spontaneously to room temperature. During the cooling precipitation of white solid took place and the suspension was stirred for 1 hour at room temperature. Filtration and drying in vacuum at 40° C. overnight produced 6.9 grams (69%) of the HBr acid addition salt of compound I. See FIG. 1 for XRPD. Elemental analysis: 3.92% N, 59.36% C, 6.16% H (theory: 3.85% N, 59.34% C, 6.09% H)

Example 1d

Preparation of Stock-Solutions of Free Base

A mixture of 500 ml ethyl acetate and 200 ml H$_2$O was added 50 grams of the HBr salt of compound I producing a two-phased slurry. To this slurry was added approximately 25 ml conc. NaOH that caused formation of a clear two-phased solution (pH was measured to 13-14). The solution was stirred vigorously for 15 minutes and the organic phase was separated. The organic phase was washed with 200 ml H$_2$O, dried over Na$_2$SO$_4$, filtered and evaporated in vacuum at 60° C. producing the free base in 38 grams yield (99%) as an almost colourless oil.

Dissolving 10 grams of the oil and adjusting the volume to 150 ml using ethyl acetate produced a 0.235 M stock-solution in ethyl acetate from which aliquots of 1.5 ml (100 mg of the free base) was used.

Dissolving 10 grams of the oil and adjusting the volume to 100 ml using 96-vol % EtOH produced a 0.353 M stock-solution in EtOH from which aliquots of 1.0 ml (100 mg of the free base) was used.

Example 1e

Formation of Salts Using Stock-Solutions of the Free Base

The given aliquots were placed in test tubes and while stirred the appropriate amount of acid was added as indicated in Table 1. If the acid was a liquid it was added neat otherwise it was dissolved in the given solvent prior to addition. After mixing and precipitation stirring was continued overnight and the precipitate collected by filtration. Before drying in vacuum at 30° C. a small reference sample was withdrawn and dried at room temperature without vacuum. This procedure was included in order to test for solvates. Some results are presented in Table 1. XRPD diffractograms are shown in FIGS. 1-22, and selected peak positions are tabulated in Table 2. Table 3 shows the solubilities of compounds of the present invention in water together with pH in the resulting saturated solution. The column "Precipitate" shows whether the precipitate isolated after the solubility determination is identical to the compound dissolved, which is indicative of the formation of hydrates.

TABLE 2

| Selected X-ray peak positions (°2θ), 2:1 means 2 bases to 1 acid. | | | | |
|---|---|---|---|---|
| Palmitate | 7.00 | 16.34 | 22.73 | 28.21 |
| Stearate | 6.70 | 15.52 | 21.81 | 28.91 |
| Lactate | 5.30 | 8.18 | 9.44 | 17.24 |
| Lactate hydrate | 11.67 | 16.70 | 18.25 | 21.76 |
| hydroxyl-isobutyrate | 5.09 | 16.60 | 20.38 | 27.37 |
| Sebacoin acid salt | 7.18 | 12.53 | 21.11 | 24.19 |
| Adipinic acid salt 2:1 | 8.03 | 13.52 | 17.90 | 24.60 |
| Adipinic acid salt 1:1 α | 9.33 | 14.01 | 18.72 | 20.63 |
| Adipinic acid salt 1:1 β | 15.69 | 21.53 | 25.81 | 31.18 |
| Glutarate 1:1 | 9.39 | 11.70 | 14.05 | 14.58 |
| Succinate 1:1 | 11.74 | 14.33 | 17.75 | 26.84 |
| Fumarate 1:1 | 8.90 | 11.47 | 19.25 | 22.33 |
| Fumarate 2:1 | 8.49 | 12.48 | 17.78 | 23.97 |
| Maleate 1:1 | 12.11 | 15.51 | 17.48 | 22.53 |
| Maleate 1:1 hydrate | 12.81 | 18.76 | 20.53 | 27.31 |
| Malonate α | 10.77 | 16.70 | 19.93 | 24.01 |
| Malonate β | 6.08 | 10.11 | 18.25 | 20.26 |
| Aspartate | 11.05 | 20.1 | 20.60 | 25.00 |
| Aspartate hydrate | 7.80 | 13.80 | 14.10 | 19.63 |
| Glutamate | 7.71 | 14.01 | 19.26 | 22.57 |
| Oxalate | 14.68 | 17.45 | 19.50 | 23.90 |
| Malate 1:1 α | 8.30 | 12.04 | 17.23 | 20.67 |
| Malate 1:1 β | 10.91 | 12.87 | 14.14 | 26.16 |
| Malate hydrate | 12.30 | 15.56 | 19.56 | 23.30 |
| D-tartrate (from EtOH) | 5.08 | 17.18 | 19.42 | 22.10 |
| Hydrochloride | 12.44 | 16.72 | 19.45 | 25.02 |
| Hydrobromide | 6.08 | 14.81 | 19.26 | 25.38 |
| Hydrobromide 1-PrOH solvate | 6.57 | 13.12 | 19.07 | 24.77 |

All values +−0.1°

TABLE 1

| Acid (Base:Acid) | MW (g/mol) | Amount of Acid (mg or μl) | Solvent | CHN (exp.) | | | CHN (theory) | | |
|---|---|---|---|---|---|---|---|---|---|
| Palmitic acid, hexadecanoic acid 1:1 | 256.42 | 90.5 | EtOAc | 75.36 | 9.77 | 2.46 | 75.64 | 9.9 | 2.6 |
| DL-Lactic acid, DL-2-hydroxypropionic acid 1:1 | 90.1 | 31.8 | EtOAc | 66.88 | 7.26 | 3.52 | 67.53 | 7.29 | 3.75 |
| Adipicacid, 1,6-hexanedioic acid 1:1 | 146.14 | 51.6 | EtOAc | 66.08 | 7.23 | 2.98 | 67.1 | 7.27 | 3.26 |
| Adipicacid, 1,6-hexanedioic acid 2:1 | 146.14 | 25.8 | EtOAc | 70.66 | 7.32 | 3.82 | 70.75 | 7.35 | 3.93 |
| Fumaric acid 1:1 | 116.01 | 40.9 | EtOH | 65.71 | 6.41 | 3.35 | 66.14 | 6.31 | 3.51 |
| Glutaric acid, 1,5-pentanedioic acid 1:1 | 132.12 | 46.6 | EtOAc | 66.09 | 6.97 | 3.2 | 66.48 | 7.03 | 3.37 |
| Malonic acid 1:1 | 104.1 | 36.7 | EtOAc | 65.04 | 6.53 | 3.54 | 65.09 | 6.5 | 3.62 |
| Oxalic acid 1:1 | 90.1 | 31.8 | EtOH | 64.28 | 6.41 | 3.61 | 64.32 | 6.21 | 3.75 |
| Sebacoinic acid, 1,8-octanedioic acid 2:1 | 202.02 | 35.6 | EtOAc | 71.79 | 7.86 | 3.58 | 71.83 | 7.86 | 3.64 |
| Succinic acid, 1,4-butanedioic acid, 2:1 | 118.1 | 20.8 | EtOAc | 65.65 | 6.86 | 3.4 | 65.80 | 6.78 (1:1 salt formed) | 3.49 |
| L-malic acid, L-2-hydroxy butanedioic acid 1:1, α | 134.1 | 47.3 | EtOAc | 62.87 | 6.20 | 3.22 | 63.29 | 6.52 | 3.36 |
| L-malic acid, L-2-hydroxy butanedioic acid 1:1, β | 134.1 | 47.3 | EtOH | 62.99 | 6.66 | 3.13 | 63.29 | 6.52 | 3.36 |
| D-tartaric acid, D-2,3-dihydroxy butanedioic acid 1:1 | 150.1 | 53.0 | EtOH | 60.67 | 6.4 | 3.07 | 60.95 | 6.28 | 3.23 |
| L-aspartic acid 1:1 | 133.1 | 47.0 | EtOH | 59.31 (contains excess of acid) | 6.7 | 7.1 | 63.43 | 6.78 | 6.73 |
| Glutamic acid 1:1 | 165.15 | 58.3 | EtOH | 56.38 (contains excess of acid) | 6.88 | 7.35 | 56.46 (for 1:1-salt and acid-monohydrate 1:1) | 6.94 | 7.06 |
| Citric acid 2:1 | 192.13 | 33.9 | EtOAc | 65.93 | 6.72 | 3.44 | 66.46 | 6.64 | 3.69 |
| HCl/Et₂O 1:1 | 2 M | 176.4 | EtOH | | | | | | |
| Phosphoric acid 1:1 | 14.7 M | 24.0 | EtOAc | 55.79 | 6.47 | 3.43 | 56.68 | 6.34 | 3.67 |

TABLE 3

| Acid (Base:Acid) | Solubility (mg/ml) | Resulting pH | Precipitate |
|---|---|---|---|
| Palmitic acid, hexadecanoic acid 1:1 | 0.4 | 8.6 | =start |
| DL-Lactic acid, DL-2-hydroxypropionic acid 1:1 | >150 | 6.1 | =start (after evaporation) |
| Adipicacid, 1,6-hexanedioic acid 1:1 | 2.5 | 4.0 | Partly 2:1 salt |
| Adipicacid, 1,6-hexanedioic acid 2:1 | 1.0 | 7.8 | =start |

TABLE 3-continued

| Acid (Base:Acid) | Solubility (mg/ml) | Resulting pH | Precipitate |
|---|---|---|---|
| Fumaric acid 1:1 | 0.2 | 3.3 | =start |
| Glutaric acid, 1,5-pentanedioic acid 1:1 | 13 | 4.6 | =start |
| Malonic acid 1:1 (α) | 5.2 | 4.0 | =new form (β) |
| Oxalic acid 1:1 | 1.1 | 2.7 | =Start |
| Sebacoinic acid, 1,8-octanedioic acid 2:1 | 0.7 | 5.5 | =Start |
| Succinic acid, 1,4-butanedioic acid, 2:1 | 2.0 | 4.0 | Hydrate |
| L-malic acid, L-2-hydroxy butanedioic acid 1:1, β | 2.8 | 4.0 | Hydrate |
| D-tartaric acid, D-2,3-dihydroxy butanedioic acid 1:1 | 1.8 | 3.5 | Hydrate |
| L-aspartic acid 1:1 | 39 | 4.3 | Hydrate |
| Glutamic acid 1:1 | >35 | 4.6 | — |
| Citric acid 2:1 | 0.5 | 4.7 | =Start |
| Phosphoric acid 1:1 | 6.0 | 2.0 | ? |
| HCl | 4.5 | 6.8 | =Start |
| HBr | 2.4 | 7.0 | =Start |

Example 2

5-HT$_{3A}$ Receptor Antagonism

In oocytes expressing human-homomeric 5-HT$_{3A}$ receptors 5-HT activates currents with an EC$_{50}$ of 2600 nM. This current can be antagonised with classical 5-HT$_3$ antagonists such as ondansetron. Ondansetron displays a Ki value below 1 nM in this system. Compound I exhibits potent antagonism in low concentrations (0.1 nM-100 nM) (IC$_{50}$~10 nM/Kb~2 nM) and agonistic properties when applied in higher concentrations (100-100000 nM) (EC$_{50}$~2600 nM) reaching a maximal current of approximately 70-80% of the maximal current elicited by 5-HT itself. In oocytes expressing rat-homomeric 5-HT$_{3A}$ receptors 5-HT activates currents with an EC$_{50}$ of 3.3 μM. The experiments were carried out as follows. Oocytes were surgically removed from mature female Xenepus laevis anaesthetized in 0.4% MS-222 for 10-15 min. The oocytes were then digested at room temperature for 2-3 hours with 0.5 mg/ml collagenase (type IA Sigma-Aldrich) in OR2 buffer (82.5 mN NaCl, 2.0 mM KCl, 1.0 mM MgCl$_2$ and 5.0 mM HEPES, pH 7.6). Oocytes avoid of the follicle layer were selected and incubated for 24 hours in Modified Barth's Saline buffer [88 mM NaCl, 1 mM KCl, 15 mM HEPES, 2.4 mM NaHCO$_3$, 0.41 mM CaCl$_2$, 0.82 mM MgSO$_4$, 0.3 mM Ca(NO$_3$)$_2$] supplemented with 2 mM sodium pyruvate, 0.1 U/l penicillin and 0.1 μg/l streptomycin. Stage IV-IV oocytes were identified and injected with 12-48 nl of nuclease free water containing 14-50 pg of cRNA coding for human 5-HT$_{3A}$ receptors and incubated at 18° C. until they were used for electrophysiological recordings (1-7 days after injection). Oocytes with expression of human 5-HT$_3$ receptors were placed in a 1 ml bath and perfused with Ringer buffer (115 mM NaCl, 2.5 mM KCl, 10 mM HEPES, 1.8 mM CaCl$_2$, 0.1 mM MgCl$_2$, pH 7.5). Cells were impaled with agar plugged 0.5-1 MΩ electrodes containing 3 M KCl and voltage clamped at −90 mV by a GeneClamp 500B amplifier. The oocytes were continuously perfused with Ringer buffer and the drugs were applied in the perfusate. 5-HT agonist-solutions were applied for 10-30 sec. The potencies of 5-HT$_3$ receptor antagonists were examined by measuring concentration-response against 10 μM 5-HT stimulation.

Example 3

Effect on Neuropatic Pain

To demonstrate an efficacy against neuropathic pain, compound I was tested in the formalin model of neuropathic pain [Neuropharm., 48, 252-263, 2005; Pain, 51, 5-17, 1992]. In this model, mice receive an injection of formalin (4.5%, 20 μl) into the plantar surface of the left hind paw and afterwards are placed into individual glass beakers (2 l capacity) for observation. The irritation caused by the formalin injection elicits a characteristic biphasic behavioural response, as quantified by the amount of time spent licking the injured paw. The first phase (~0-10 minutes) represents direct chemical irritation and nociception, whereas the second (~20-30 minutes) is thought to represent pain of neuropathic origin. The two phases are separated by a quiescent period in which behaviour returns to normal. Measuring the amount of time spent licking the injured paw in the two phases assesses the effectiveness of test compounds to reduce the painful stimuli.

Eight C57/B6 mice (ca. 25 g) were tested per group. Table 4 below show the amount of time spent licking the injured paw in the two phases, i.e. 0-5 minutes and 20-30 minutes post formalin injection. The amount of compound administered is calculated as the free base.

TABLE 4

|  | Vehicle | 1.0 mg/kg | 2.5 mg/kg | 10 mg/kg |
|---|---|---|---|---|
| 0-5 minutes (sec) | 42 | 37 | 30 | 37 |
| 20-30 minutes (sec) | 41 | 43 | 26 | 6 |

The data in table 4 shows that compound I has little effect in the first phase representing direct chemical irritation and nociception. More notably, the data also show a clear and dose dependent decrease in the time spent licking paws in the second phase indicating an effect of the compound of the present invention in the treatment of neuropathic pain.

Moreover, the potential analgesic effects of compound I in an animal model of neuropathic pain were assessed. A peripheral mononeuropathy was induced in the right hind limb of rats following a chronic constriction nerve injury, and the development of mechanical allodynia and thermal hyperalgesia was monitored using established behavioural tests (Von Frey filaments and the Hargreaves Plantar Device, respectively). Subcutaneous administration of compound I at dose of 1.9, 4.8 and 7.9 mg/kg in 10% hydroxypropyl-betacyclodextrin did not increase the paw withdrawal threshold of the right hind paw when challenged with Von Frey filaments. However, significant increases in paw withdrawal latency were seen at 4.8 and 7.9 mg/kg in thermal hyperalgesia, indicating an analgesic response.

The invention claimed is:

1. A method for the treatment of irritable bowel syndrome, the method comprising administering a therapeutically effective amount of 4-[2-(4-methylphenylsulfanyl)phenyl]piperidine or a pharmaceutically acceptable salt thereof (compound I) to a patient in need thereof.

2. The method according to claim 1, wherein compound I is administered in a crystalline form.

3. The method according to claim 2, wherein compound I is the HBr addition salt.

4. The method according to claim 3, wherein the HBr addition salt is characterised by peaks in an XRPD at approximately 6.08, 14.81, 19.26 and 25.38° 2θ (all ±0.1°).

5. The method according to claim 4, wherein said HBr addition salt is characterised by an XRPD as depicted in FIG. 1.

6. The method according to claim 1, wherein compound I is administered at 1-20 mg/day.

* * * * *